United States Patent [19]

Vijayan et al.

[11] Patent Number: 5,047,054
[45] Date of Patent: Sep. 10, 1991

[54] TRIAZINE RESIN COATED PROSTHETIC IMPLANTS

[75] Inventors: Kandasamy Vijayan, Memphis; Larry H. Strait, Jr., Cordova; Russell D. Jamison, Germantown, all of Tenn.

[73] Assignee: Smith & Nephew Richards, Inc., Memphis, Tenn.

[21] Appl. No.: 599,299

[22] Filed: Oct. 17, 1990

[51] Int. Cl.⁵ .............................................. A61F 2/28
[52] U.S. Cl. ....................................... 623/16; 623/22
[58] Field of Search ................... 623/16, 22; 433/228.1

[56] References Cited

U.S. PATENT DOCUMENTS 4,356,571 11/1982 Esper et al. ............................ 623/22
4,535,487 8/1985 Esper et al. ............................ 623/18

Primary Examiner—Randall L. Green
Assistant Examiner—Stephanie L. Iantorno
Attorney, Agent, or Firm—Pravel, Gambrell, Hewitt, Kimball & Krieger

[57] ABSTRACT

The invention provides biocompatible, corrosion-resistant prostheses and methods for producing these. A coating comprising a bismaleimide-triazine resin, a biocompatible plasticizer and optionally a thickener is applied to a prosthesis substrate and the resin is cured to provide a tightly adherent, biocompatible, corrosion-resistant coating. Radio-opaque materials, such as barium sulfate, may be included in the coating as well as bone ingrowth materials such as hydroxyapatite.

16 Claims, 4 Drawing Sheets

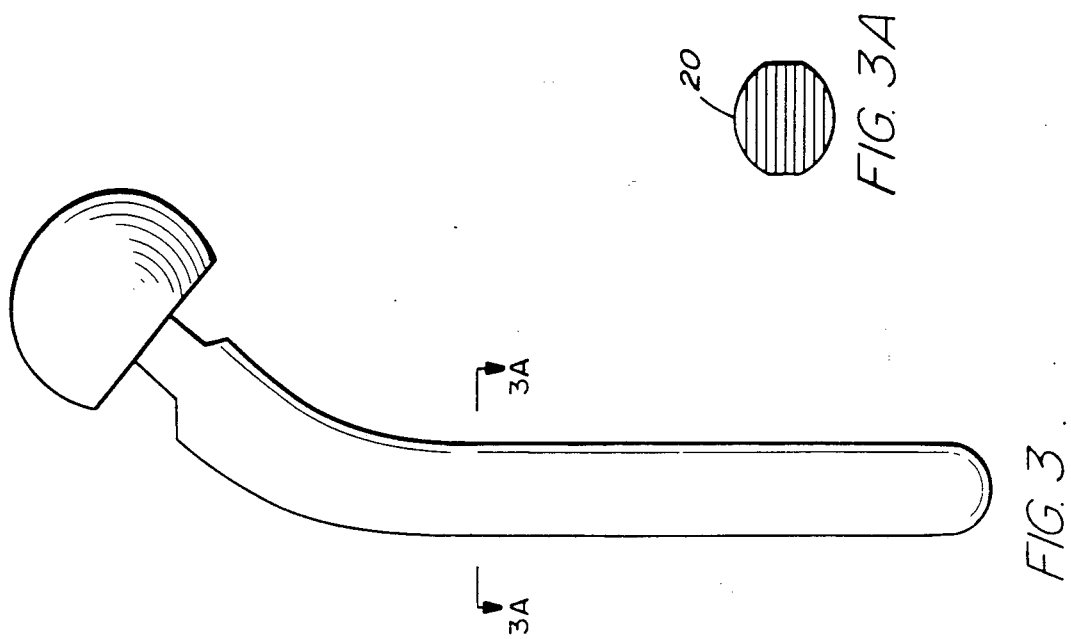
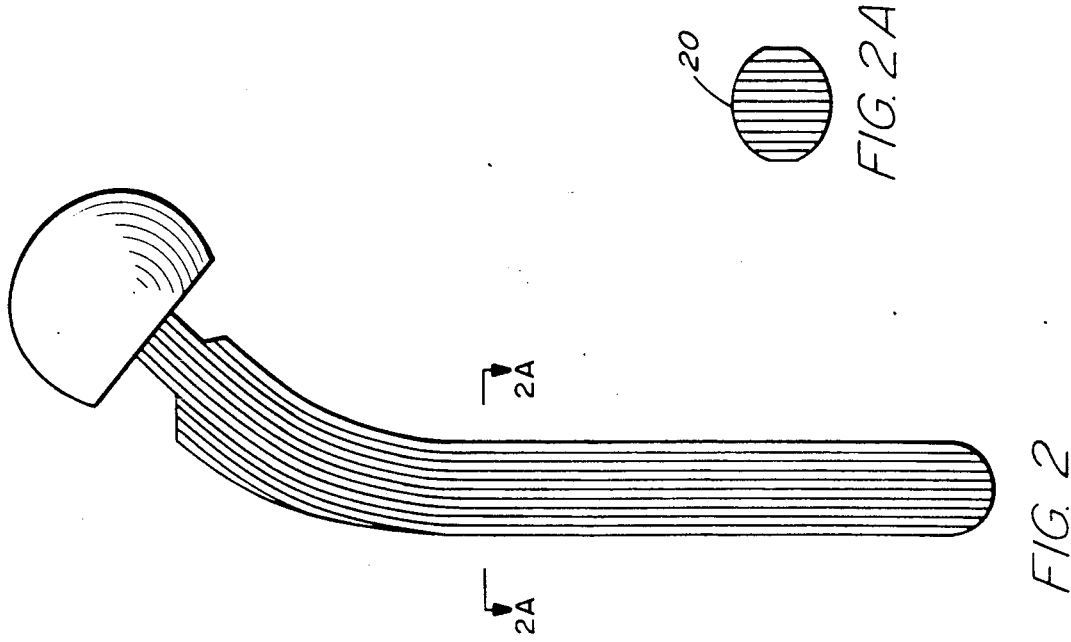

TRIAZINE RESIN COATED PROSTHETIC IMPLANTS

BACKGROUND

1. Field of the Invention

This invention relates to biocompatible coatings for orthopedic implants. The invention coating shields the implant material from corrosive bodily fluids and prevents the gradual leaching or ionization of the implant substrate material into surrounding body tissue.

2. Background of the Invention

Orthopedic implants are currently manufactured from a variety of materials, most commonly metals, metal alloys and ceramics. The use of polymers and composites is still in its infancy but is expected to increase. Apart from the mechanical strength and modulus requirements that an implant material must possess to provide useful implants with reasonable life spans, the implant material must also be compatible with body tissue. Further, the implant material should be resistant to the corrosive or leaching action of body fluids.

Substrate materials such as metals and their alloys ( collectively referred to hereafter as "metals") possess the necessary strength for use as orthopedic implants. However, metals generally have a higher modulus of elasticity than bone. Consequently, when metallic implants are used in a load-bearing function, the load is not always effectively transferred to the bone. This could result in gradual bone resorption, which can have serious effects, especially in the case of young implant recipients. Over a period of time, the degree of bone resorption could result in loosening of the implant necessitating surgery to perform remedial action such as a replacement prosthesis.

Metals are not completely inert in the body but are generally prone to corrosion by ionization in body fluids. This ionization can be acute when a metallic prosthesis articulates against an opposing surface. The articulating action repeatedly clears the surface of any passive oxide film that might develop on the surface and continually exposes fresh metallic surface to the body fluids.

It has been suggested that metallic implants can be coated to improve their tissue compatibility by reducing or preventing ionization corrosion. Thus, for instance, U.S. Pat. No. 4,145,764 to Suzuki et al. recognized that while metal prostheses have excellent mechanical strength, they tend to corrode in the body by ionization. To solve this problem, Suzuki proposed a metal prosthesis plasma sprayed with a bonding agent which is in turn covered with a porous ceramic coating which would allow the ingrowth of bone spicules into the pores. This combination, Suzuki claimed, would provide both the mechanical strength of metals and the biocompatibility of ceramics.

Suzuki did not, however, address the issue of dimensional changes that occur when applying a coating or the effect of these dimensional changes in the tightness of fit between the surfaces of an articulating joint prosthesis. Further, the application of ceramic coatings to metal substrates often results in non-uniform, poorly-bonded coatings which tend to crack due to differences in thermal expansion between the ceramic and the underlying metal substrate. Furthermore, such coatings are relatively thick (50-300 microns) and since the bond between the metal and the ceramic coating is often weak, there is always the risk of galling or separation of the ceramic coating.

U.S. Pat. No. 4,164,794 to Spector et al. relates to prosthetic devices fabricated from or coated with selected thermoplastics referred to as "bioengineering thermoplastics." The prostheses have an inner load bearing portion and an outer sintered or foamed porous coating of a bioengineering thermoplastic. The coatings are 0.5 to 10 mm thick and the average pore diameter is 90-600 microns. The function of the pores is apparently to allow ingrowth of bone spicules to stabilize the implant in the body, with no recognition that there could be any benefit in preventing ionization of substrate materials.

Polymeric prostheses with substrates formed of thermoplastics such as high density polyethylene (HDPE) have been tried, but are not as biocompatible as originally assumed according to U.S. Pat. No. 4,356,571. According to this it has been found that over a long period of time a layer of connective tissue can form on the HDPE surface. This layer may be such as to cause loosening of the implant so that reimplantation or other remedial action becomes necessary. Further, according to the '571 patent, it has been found that thermoplastics generally are not as passive to body fluids as originally thought. Body fluids can invade the thermoplastic composition by a leaching or diffusion action resulting in a weakening of the implant. Further, the leaching action releases the implant composition into the body in small quantities, with unknown long term effects.

Further, according to U.S. Pat. No. 4,356,571, it was generally believed that thermosetting resins could not be used as implant materials because they would always release substances that were not biocompatible. The Esper patent is directed to prosthetic implants produced entirely of cured fiber reinforced composites of a biocompatible, thermosetting "triazine resin."

Recent studies suggest that carbon fiber composites may exhibit significantly higher electrochemical activity than metal alloys due to the high electrical conductivity of carbon fibers and the absence of an electrically resistant oxide layer such as those spontaneously formed over metal alloys. While clinical effects of this conductivity are not yet known, it has been suggested that these electrical interactions are undesirable.

In view of the unique advantages of each of the many different types of materials in the fabrication and use of prosthetic devices, there exists a need for a means of coating an implant formed, for example, of thermoplastic, metallic or composite materials to render it inert in the body. Such a coating must be of a type that would render a metallic or composite implant immune to corrosion by ionization and a thermoplastic, metallic or composite implant immune to corrosion, leaching and invasion by bodily fluids.

BRIEF DESCRIPTION OF THE DRAWINGS

FIGS. 2 and 2a are schematic diagrams of a composite hip stem showing the alignment of prepregs.

FIGS. 3 and 3a are schematic diagrams of a composite hip stem showing the alignment of prepregs.

SUMMARY OF THE INVENTION

The invention provides a biocompatible, corrosion-resistant coating for application to the surface of any type of substrate including those formed of thermoplastic, metal, metal alloy, composite or ceramic orthopedic implants. The coating of the invention is biocompatible and corrosion-resistant and is formed at least in part of a thermosetting bismaleimide-triazine resin ("BT resin") and a biocompatible plasticizer.

The corrosion-resistant orthopedic implants of the present invention may be produced by any of the conventional techniques, such as for example by machining, casting or lamination. The surface is coated with a thin layer of a composition of a BT resin and a biocompatible plasticizer. The coating can be carried out by any known method for coating implants, such as dipping, spraying and the like. The implant is then subjected to heat treatment to allow the thermosetting BT resin to cure and provide a tightly adherent, biocompatible, corrosion-resistant skin or coating over the substrate surface.

The coating composition which includes triazine and a biocompatible plasticizer, may optionally include a thickening agent. The thickening agent increases the viscosity of the hot (80°–100° C.) mixture of resin and plasticizer and permits the formation of a thicker coating on the substrate.

As a further advantage, the coating can include an additive such as barium sulfate so the prostheses can be made opaque to X-rays as an aid to diagnosticians. Thus, while the typical thermoplastic implant is X-ray transparent, a coating of BT resin including such an additive would render the implant radio-opaque.

Other useful additives are also readily added to the BT resin coating. For instance, the inclusion of hydroxyapatite particles could be used to form a base for the ingrowth or adherence of adjacent tissue to assist in stabilizing the coated implant in the body.

DETAILED DESCRIPTION OF THE PREFERRED EMBODIMENTS

In accordance with the invention, corrosionresistant, biocompatible prostheses are produced by coating a conventional prosthesis formed of metal, metal alloy, composite materials, ceramics or thermoplastic materials with a composition formed at least in part of bismaleimide-triazine resin, and optionally a biocompatible plasticizer and a thickening agent and then at least partially curing the resin.

Figure 1:
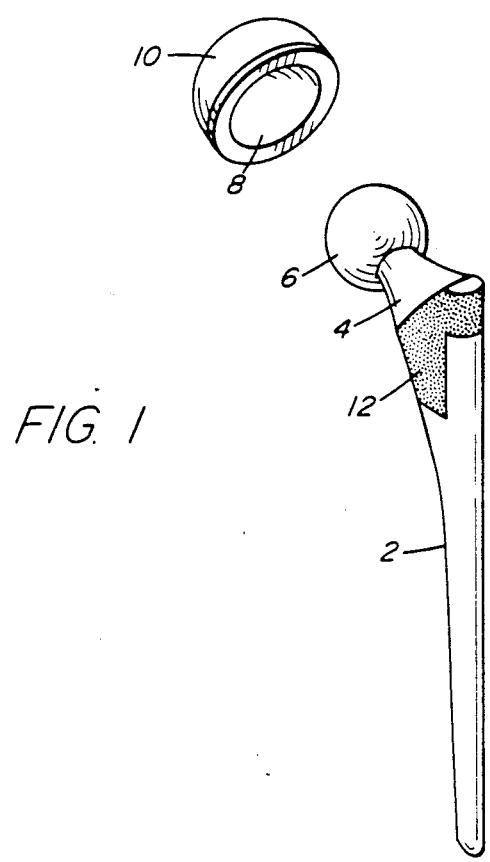
FIG. 1 is a schematic diagram of a hip stem.

While the invention coating may be applied to any orthopedic implant, typical load-bearing implants are shown in FIGS. 1–3. FIG. 1 shows a typical hip stem 2 having a neck 4, onto which a femoral head 6 is attached. The hip stem shown is partially coated with a porous bead coating 12 and has a matching acetabular cup 10 fitted with an ultra high density polyethylene lining 8. FIGS. 2 and 3 show composite hip joint stems fabricated by laminating together carbon fiber mats preimpregnated with a thermoplastic resin. These "prepregs" 20 may be aligned as shown in FIGS. 2 and 2a or as in FIGS. 3 and 3a. FIGS. 2a and 3a are cross sectional views, taken along A—A of FIGS. 2 and 3 respectively, and show more clearly the parallel arrangement of the prepregs 20. Upon machining the laminated composites of FIGS. 2 and 3 into shape, the carbon fiber at the edges of the prepregs become exposed. Thus, upon implantation, the surrounding body tissue will be exposed to carbon fiber unless the stem is covered with a durable biocompatible protective coating.

The invention coatings are tightly adherent to thermoplastics, metals (including their alloys) and ceramics. It is of particular interest that the coatings are adherent to the polyaryletherketone family, i.e. polyetheretherketone, polyetherketone, polyetherketoneketone and the like. Thus, the invention coating may be readily used on composite prostheses that include these compositions as the thermoplastic component.

Bismaleimide-triazine resin ("BT resin") is a generic name for a highly heat resistant group of thermosetting resins having two main constituents: bismaleimide and triazine. BT resins are highly reactive and contain an active unsaturated triple bond —O—C≡N (cyanato). The BT resin commercially available as BT 2160 RX from Mitsubishi Gas Chemical Co. is preferred although other BT resins are also useful. A booklet entitled "High Heat Resistant BT Resin" 4th ed. (1984) published by the commercial manufacturer of BT resins, Mitsubishi Gas Chemical Co., incorporated by reference as if fully set forth, gives further details of the properties of this resin.

BT resin can be modified by the addition of a range of other resins. A non-exclusive list of such resins includes epoxy resin, acrylic resin, meta acrylic resin, silicone resin, acrylepoxy resin, silicone-epoxy resin, alkyd resin, polyester resin, polyurethane resin, phenolic resin, melamine resin, urea resin, xylene resin, phenol modified xylene resin, imide resin, polybutadiene resin, diallyl phthalate resins, polybutene resin, cyclopentadiene resin, rubber, thermoplastic resin, polyvinylbutyral resins, etc. Modification by addition of additives other than resin, inorganic filler, pigment, or dyestaff is also possible.

The plasticizers useful in the present invention are those that are (i) biocompatible and (ii) compatible with BT resin and the substrate. These plasticizers include for example, citric acid esters and glyceryl esters. The useful citric acid esters include acetyltri-n-butyl citrate, acetyltriethyl citrate, tri-n-butyl citrate, n-butyl phthalyl-n-butyl glycolate, triethyl citrate, acetyltri-n-hexyl citrate, n-butyltri-n-hexyl citrate, tri-n-hexyl trimellitate, monostearyl citrate, and the like. Such plasticizers are produced by Morflex Chemical Co. of Greensboro, N.C. under a variety of trade names. The pamphlet, "Citrate Esters as Plasticizers for Aqueous-Based Pharmaceutical Coatings," published by Morflex is hereby incorporated by reference as if fully set forth. The useful glyceryl esters include oligomers, such as oligo(L-lactate-co-glycerate) and oligo(glycolate-co-glycerate) which are of low molecular weight and biodegradable. Since these glyceryl ester oligomers are biodegradable, they may improve stability of the implant by allowing bone ingrowth into the coated surface. Oligomers of this type are commercially available from Boehringer Ingelheim.

The BT resin/plasticizer composition may advantageously be prepared by heating the resin to 80°–100° C. and mixing with the appropriate quantity of plasticizer. This mixing with a plasticizer results in a reduction in the resin viscosity so that it is more easily processible, i.e. more easily used to form a coating. Coating compositions may contain from about 0 wt. % to about 20 wt. %, or more, plasticizer but it is preferred that plasticizer be added in the range from about 10 to about 20 wt. %, based on the total weight of the coating composition.

The viscosity of the BT resin/plasticizer coating composition may become very low at high (80°-100° C.) temperature. In this instance, a biocompatible thickening agent should be incorporated into the composition to permit the formation of a suitably thick coating on the substrate. These thickening agents may be selected from sodium carboxymethylcellulose, methyl cellulose, hydroxypropyl methylcellulose, carboxymethyl methylcellulose, hydroxyethyl methylcellulose, hydroxypropyl cellulose, hydroxyethyl cellulose, hydroxypropyl hydroxyethylcellulose, carboxymethyl hydroxyethylcellulose, guar gum, hydroxypropyl guar, carboxymethyl hydroxypropyl guar, and the like. These cellulose derivatives are in wide use in the food industry and are obtainable from, for instance, Aqualon Company. The quantity of thickening agent added will vary depending upon the initial viscosity of the BT resin/plasticizer mixture and the final viscosity desired. Typically, about 2 wt. % thickening agent is added, based upon the total weight of the coating composition.

As an added benefit, since the cellulose-derived thickening agents are biodegradable, they will over a period of time be absorbed out of the coating into the body leaving spaces into which bone ingrowth can take place. This ingrowth assists in stabilizing the implant in the skeletal structure.

The BT resin/plasticizer coating composition can be applied by dipping the prosthesis in the hot, 80°-100° C., melt composition of triazine resin or triazine resin and plasticizer or triazine resin, plasticizer and thickening agent; spraying the prosthesis with the composition or any other convenient method. Once the prosthesis is covered with a film of coating composition, the resin may be cured by heating, for instance, according to the curing curves of FIG. 4 preferably in an oxygen-free atmosphere. In order to produce an even harder coating, the coated prosthesis may be heated even further to 230° C. for about 24 hours. In general, BT resin can be heated to 160°-300° C. in order to crosslink the molecules. However, the plasticizer may have a lower temperature limit. Thus, for instance, if a plastiCizer selected decomposes at about 250° C., it is advisable to cure the BT resin at a temperature lower than 250° C. to avoid plasticizer decomposition. It is also not advisable to heat the coating rapidly during the drying phase because BT resin monomer may evaporate from the surface. Thus, it is preferred that a curing curve similar to the curves of FIG. 4 be followed to first allow preliminary (B-stage) polymerization to take place followed by crosslinking. Thereafter, the BT resin may preferably be heated up to about 230° C. to allow further hardening (crosslinking) to take place.

Further, in cooling the cured coating, care should be exercised to avoid cracking the coating or causing it to spall or separate from the substrate due to uneven contraction rates between substrate and coating. Thus, slow cooling to room temperature over a period of hours is preferred.

Figure 4:
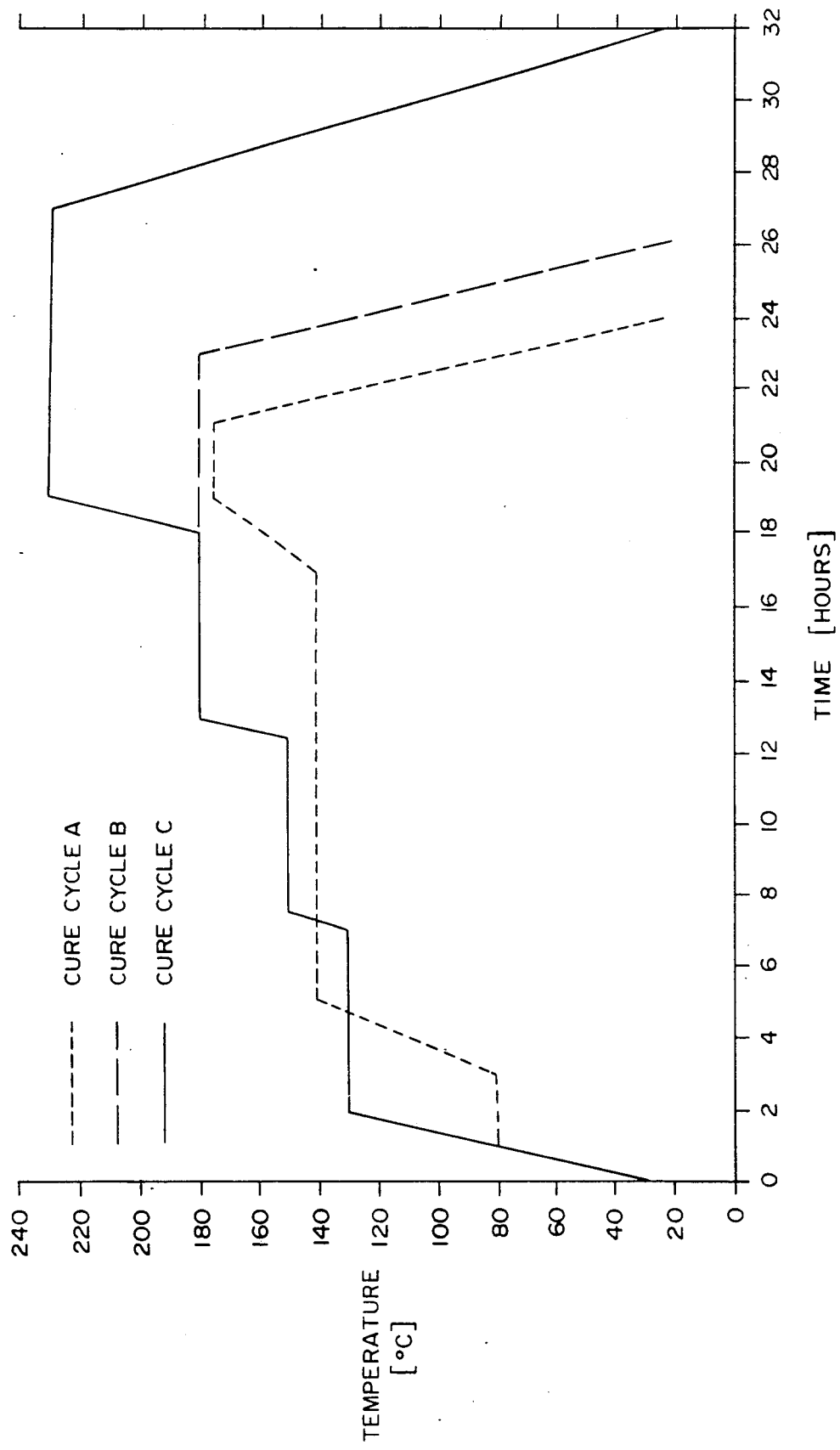
FIG. 4 shows cure cycles useful for curing the invention coating.

Clearly, possible curing cycles are not limited to those of FIG. 4 but may vary widely. However, in each case it is preferable to heat up slowly at first to avoid resin monomer loss due to boil off and to B-stage the resin, to then maintain at a temperature that allows crosslinking to take place and finally to cool slowly to avoid spalling of the coating.

Using an appropriate method of application, a coating of any desired thickness may be obtained. However, it is preferred that the coating thickness be in the range from about 0.025 to about 0.500 mm. To apply the coating, for instance, the substrate may be first dipped in a low viscosity resin/plasticizer composition to form a thin coating which is then dried. The dried, coated substrate may then be redipped to provide a thicker coating or may be redipped into a composition containing additives such as a radio-opaque component and/or hydroxyapatite or $\beta$-tricalcium phosphate. Alternatively, the substrate may be dipped into a relatively more viscous resin/plasticizer/thickening agent composition to obtain a thicker coating. This more viscous composition may contain additives such as bone ingrowth promoters and/or radio opacity enhancers. The BT resin and biocompatible plasticizer coating may be applied to prostheses produced by conventional process with minimal surface preparation. In the case of metallic or thermoplastic-based prosthesis substrates, it is preferred that the surface be roughened by, for instance, rubbing with coarse sandpaper to provide a surface to which the resin can bond more readily. Further, the surfaces to be coated should be clean and free of grease or other foreign matter.

As mentioned before, in preparing the BT resin/plasticizer coating solution, other ingredients such as barium sulfate, hydroxyapatite, $\beta$-tricalcium phosphate, and the like may be added if needed for specific purposes. For example, the addition of powdered barium sulfate can provide a coating with barium sulfate dispersed throughout. A thermoplastic prosthesis coated with such a composition is radio-opaque so that a diagnostician can readily determine its location and condition in the body. It is also possible to determine mechanical failure of the prosthesis more readily by X-ray techniques rather than invasive surgery if the prosthesis is radio-opaque.

A coating with a material such as hydroxyapatite or $\beta$-tricalcium phosphate dispersed throughout, for example, could be used to make the coated prosthesis more conducive to tissue adherence or ingrowth depending on the type of hydroxyapatite used. A dense hydroxyapatite has a roughened outer surface to which tissue adheres easily, and which as a porous material accommodates ingrowth of surrounding tissue.

Coatings with uniform dispersions of other solid materials are also readily produced by mixing and dispersing the powdered form of the solid material in the coating solution of BT resin, plasticizer and optionally a thickening agent. Of course, the powdered material could be added in a subsequent step by blowing powder onto the wet coating. This, however, will probably not provide a very uniform dispersion of the powder composition in the coating.

In order to promote wetting of the substrate with the coating composition, an optional wetting agent may be added. Such agents are known in the art and include mineral oil and the like which are typically added about less than 1 wt. % based upon the total weight of the coating composition.

The following examples serve to illustrate the invention and are not intended to limit the scope of the invention as described above and claimed hereafter.

EXAMPLE 1

The Application of a Triazine Resin/ Hydroxyapatite Coating to a Metallic Hip Implant Hydroxyapatite coatings are being considered for use on metallic implants to improve the fixation of implants to the bone.

A Ti-6A1-4V hip stem was cleaned with acetone in an ultrasonic cleaner and stored in a desiccator.

Two separate triazine resin coating compositions were prepared. In the first composition, for use in the base coating, BT 2160 RX resin from Mitsubishi Gas Chemical Co. was heated to 90° C. then degassed in a vacuum desiccator. In the second composition, for use in subsequent coatings, BT 2160 RX was heated to 90° C. and hydroxyapatite (HA) powder was mixed into the liquified resin in the volume ratio HA:resin::1:5. The mixture was stirred under heat for approximately 10 minutes after which the mixture was degassed in a vacuum desiccator. Both compositions were stored in sealed containers at −10° C. prior to use.

Figure 5:
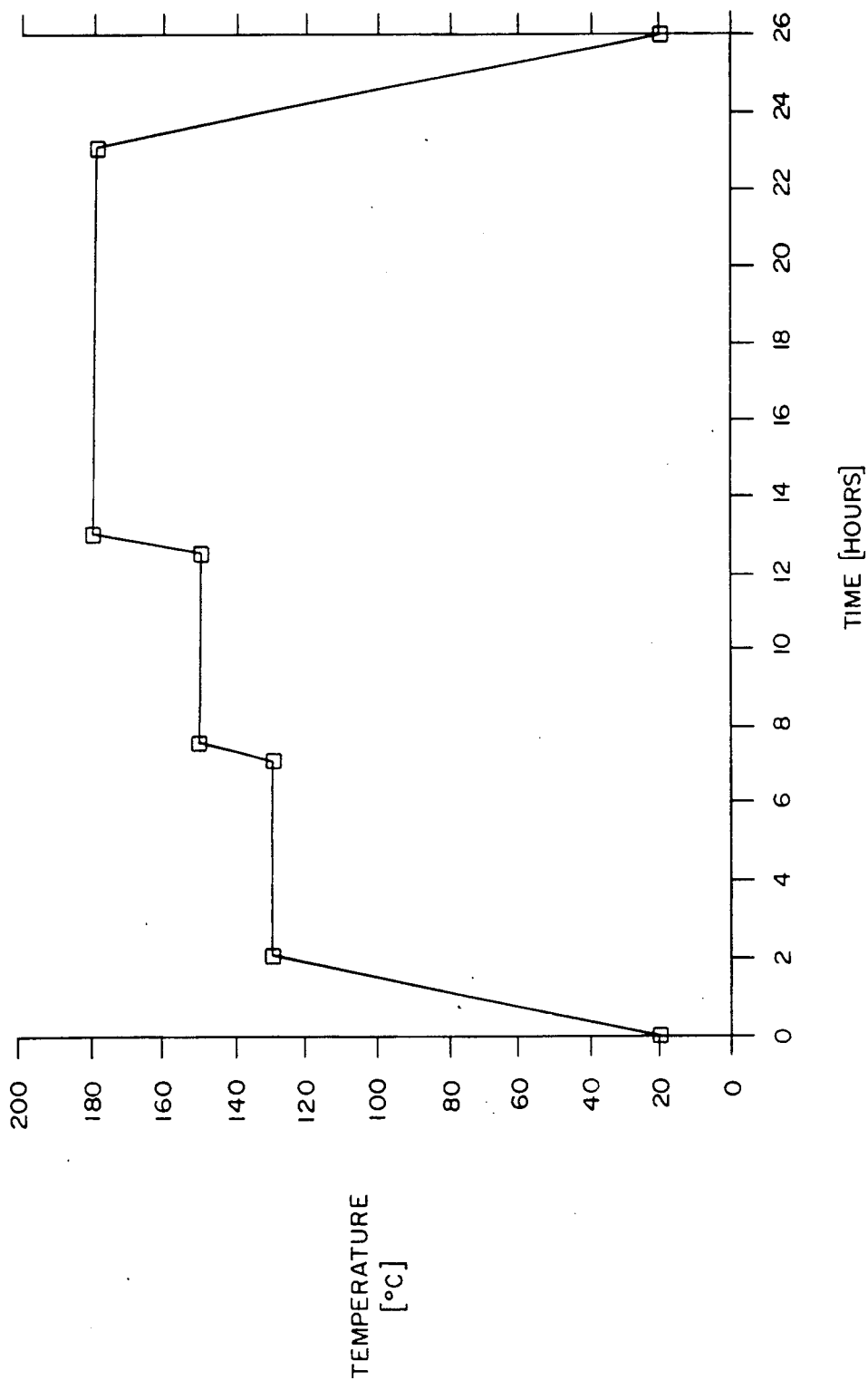
FIG. 5 shows a cure cycle useful for curing the invention coating.

To apply the coatings, the resin composition was first heated to about 90° C. and the stem was placed in a shallow dish. Hot resin was then poured over the stem to cover it, except for the trunnion. The stem was rotated several times to remove entrapped air and then removed from the dish, suspended from a rack by the trunnion and placed in an oven for curing the resin according to the cure cycle of FIG. 5. As the temperature in the oven increased during the initial portion of the cure cycle, the resin became less viscous, so that some of the resin dripped from the hip stem, until the resin began to gel. This procedure provided a consistent, uniform coating thickness over the surface as determined by optical microscopy. One base coat of pure triazine resin and three coats of HA/triazine resin were applied to the stem. After the application of the first HA/resin coat, visual inspection at 8× magnification showed a coating similar in texture to 320 grit sandpaper with particles mostly uniformly distributed but with some minor agglomeration. After the second and third coatings with HA/resin, the coating appeared the same albeit with increasing particle concentration after each coating. Multiple HA/resin coatings were used only to obtain an acceptable coating thickness. However, only the final coating need be with a HA/resin composition if an optional thickening agent were included in the base composition to provide a thicker base coat.

Once coating was complete, the stem was cut to remove the trunnion and to remove sections 1" and 2" from the distal tip. These sections were mounted for SEM and metallographic examination while the proximal portion was prepared for a "pull-off" test to measure the strength of adherence of the coating.

Pull-off tests were conducted on a pneumatic adhesion tensile testing apparatus. Aluminum pull-stubs were bonded to flat regions of the coating on either side of the stem using Miller-Stephenson 907 2-part epoxy resin. The epoxy resin was allowed to cure in a desiccator for 48 hours before conducting the pull-off test. The first aluminum pull-stub required 1218 psi to pull it from the stem, the second required 1299 psi. In both cases failure occurred at the triazine coating/metal surface interface. It is expected that pre-treatment of the metal surface, such as by roughening the surface, will further improve the bond strength of the resin to the surface. By way of comparison, previous tests of plasma sprayed HA on Ti-6A1-4V substrates show a bond strength of about 1191±593 psi. The triazine/HA coating is therefore comparable in adherence to coatings produced by the plasma spray process.

The thickness of the coating was determined to be about 0.002" from SEM measurements taken on the sections cut from the distal tip of the stem.

EXAMPLE 2

The Coating of Composites of Polyetheretherketone (PEEK) and Carbon Fiber Mats With a Triazine Resin Composition Three separate coating compositions were prepared from BT 2160 RX resin and 20 wt. % each of a plasticizer. The plasticizers were triethyl citrate (TEC), acetyltri-n-butyl citrate (ATBC) and n-butyl/tri-n-hexyl citrate (BTHC). The coating compositions were prepared by heating the resin to 90° C. in an oven and adding 20 wt. % plasticizer and less than about 1 wt. % of a mineral oil wetting agent while maintaining the 90° C. temperature and stirring periodically for 15 minutes. The mixtures were then degassed in a vacuum desiccator. Thereafter, the mixtures were repeatedly heated to 90° C. and degassed until no bubbles were visible at 30 mm Hg.

Carbon-PEEK composite coupons measuring 1.5"×1.5"×⅛" were prepared by machining and polishing one side for coating while covering the opposite side with release tape to prevent resin coating and enable more accurate coating thickness measurement. The coatings were applied by immersing the coupons in a 90° C. coating composition, as prepared above, for about 10 seconds. The coupons were then hung on a sample rack and placed in an oven for curing according to one of the cure cycles shown in FIG. 4. To apply a second coating, the above coating steps were repeated. These steps were followed for each coating formulation except the coating including 20 wt. % BTHC. During this coating procedure, the first coat was only B-staged, not fully cured, before the second coating was applied.

To perform "pull-off" tests, aluminum pull-stubs of ½" diameter were bonded to the triazine resin coatings with 3M Scotchweld 1838 B/A epoxy which cures completely in 24 hours to a 4000 psi tensile strength. To ensure good adhesion, the pull stub surfaces were first grit blasted and cleaned with acetone in an ultrasonic cleaner.

Figure 6:
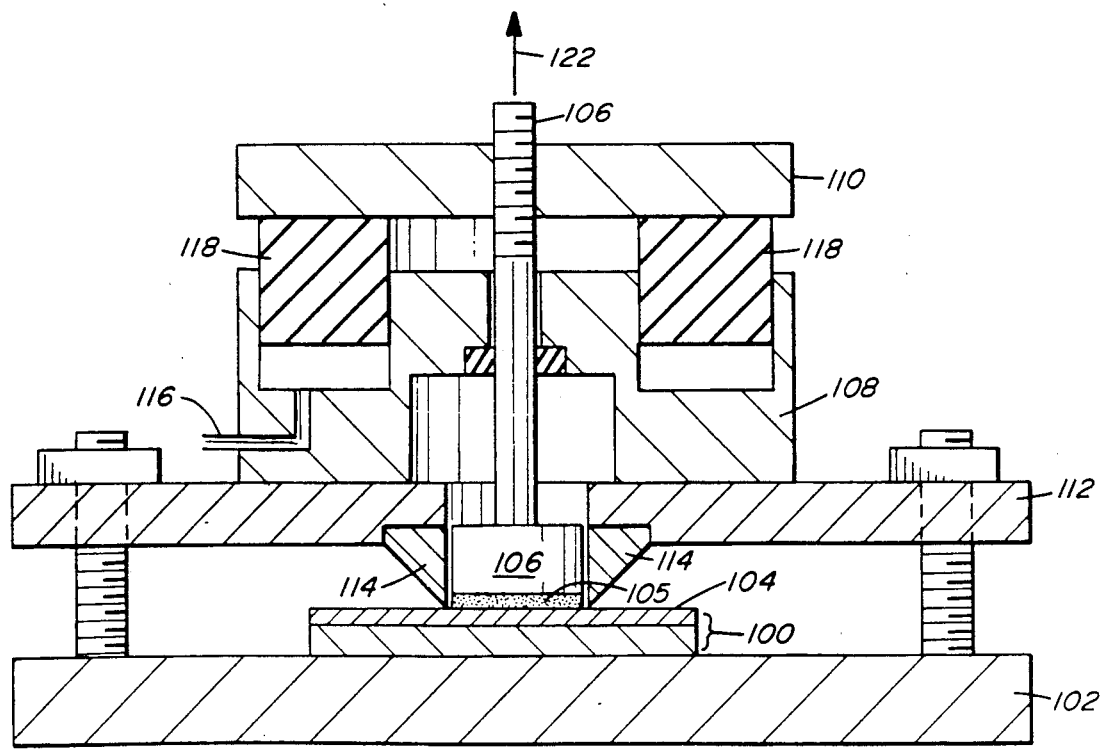
FIG. 6 is a diagrammatic cross-section of a pull-off test apparatus.

The tensile pull-off tests were conducted on a pneumatic adhesion tensile testing apparatus manufactured by SEMicro of Rockville, Md. The test was conducted according to ASTM D4541, "Pull Off Strength of Coatings using Portable Adhesion Testers." The coupons were clamped in a fixture that prevents flexing of the substrate during the test and which provides a uniform test area without the need to score the coating around the pull-stub. The test apparatus is shown in FIG. 6. The coupon 100 is placed on the base aluminum plate 102 with the coating 104 face upward. The pull-off stub 106 is attached to the coated face of the coupon 104 by means of an adhesive 105 and the aluminum pull-off stub 106 projecting upwards through a pressurizable ring 108 and a self-aligning bearing plate 110. The coupon is securely clamped in place by an upper aluminum plate 112 equipped with a steel cut-off ring 114. The upper aluminum plate 112 is clamped tightly with bolts 120 so that the cut-off ring 114 fits tightly into the coated surface 104. Gas is pressured into the pressurizable ring 108 at inlet 116, forcing gasket 118 upwards against the self-aligning bearing plate 110 and causing it to exert an upward force in direction 122 on the pull-stub 106 which is screwed into the bearing plate as shown. Thus, the strength of the bond may be measured by measuring the pressure of the gas needed to pull off the pull-stub 106. The diameter of the steel cut-off ring effectively defines the area of the coating subject to the pulling force.

The tensile pull-off strength of the coating was recorded for each coated coupon and the failure mode was noted as follows:

(1) Cohesive failure - substrate
(2) Cohesive failure - coating
(3) Cohesive failure - adhesive
(4) Adhesive failure - coating/substrate interface
(5) Adhesive failure - adhesive/coating interface
(6) Adhesive failure - stub/adhesive interface For machined composite substrates, it was often difficult to distinguish between adhesive failure of the coating/substrate (C/S) interface and cohesive failure of the substrate. For the purposes of this study, adhesive failure at the C/S interface was considered to include some pull-off of fibers from the surface of the substrate. Failure was not considered to be cohesive in the substrate unless at least half of the surface ply had been pulled away from the substrate. It should also be noted that due to the transparent nature of thin coatings of triazine resin, it was also difficult to distinguish between adhesive failure at the C/S interface and cohesive failure of the coating. However, the presence of fiber pull-off on the stub was considered to be indicative of the former failure mode rather than the latter.

The results of these tests are shown in Table I which summarizes data obtained from 30 coated coupons. The primary failure mode for nearly all of the coupons was adhesive failure of the coating/substrate interface. However, the bond strength of the coatings at 2052±98 psi compares favorably with plasma sprayed ultra high molecular weight polyethylene coatings at 1177±58 psi and plasma sprayed PEEK coatings at 1885±276 psi.

TABLE I

| Formulation | Cure Cycle | ID # | Thick. [in.] | Strength [psi] | Primary Failure Mode |
|---|---|---|---|---|---|
| Pure Triazine | A | 1 | <0.001 | 2028 | 99% Adhesive C/S |
| | | 2 | 0.002 | 2109 | 95% Adhesive C/S |
| | | 3 | 0.003 | 2191 | 99% Adhesive C/S |
| | | 4 | 0.001 | 1987 | 90% Adhesive C/S |
| | | 5 | 0.001 | 1946 | 99% Adhesive C/S |
| | | | 0.002 | 2052 ±98 | |
| Pure Triazine | B | 1 | 0.002 | 1906 | 95% Adhesive C/S |
| | | 2 | 0.002 | 1702 | 99% Adhesive C/S |
| | | 3 | 0.001 | 2231 | 99% Adhesive C/S |
| | | 4 | <0.001 | 2028 | 60% Adhesive A/C |
| | | 5 | 0.001 | 1621 | 85% Adhesive C/S |
| | | | 0.001 | 1898 ± 246 | |
| Pure Triazine | C | 1 | 0.003 | 1906 | 75% Adhesive C/S |
| | | 2 | 0.001 | 1906 | 75% Adhesive A/C |
| | | 3 | 0.002 | 1498 | 90% Adhesive A/C |
| | | 4 | 0.004 | 1498 | 70% Adhesive C/S |
| | | 5 | 0.002 | 1824 | 99% Adhesive A/C |
| | | | 0.002 | 1718 ± 222 | |
| 20 Wt. % TEC | B | 1 | 0.001 | 1824 | 95% Adhesive C/S |
| | | 2 | 0.001 | 1539 | 99% Adhesive C/S |
| | | 3 | 0.001 | 1906 | 95% Adhesive C/S |
| | | 4 | 0.002 | 1987 | 95% Adhesive C/S |
| | | 5 | 0.002 | 1906 | 60% Cohesive Substrate |
| | | | 0.001 | 1832 ± 174 | |
| 20 Wt. % ATBC | B | 1 | 0.001 | 1987 | 95% Adhesive C/S |
| | | 2 | 0.001 | 1906 | 95% Adhesive C/S |
| | | 3 | 0.001 | 1906 | 99% Adhesive C/S |
| | | 4 | 0.001 | 2028 | 95% Adhesive C/S |
| | | 5 | <0.001 | 1376 | 99% Adhesive C/S |
| | | | 0.001 | 1841 ± 265 | |
| 20 Wt. % BTHC | B | 1 | 0.002 | 1336 | 65% Adhesive C/S |
| | | 2 | 0.003 | 1580 | 99% Adhesive C/S |
| | | 3 | 0.004 | 1946 | 70% Adhesive C/S |
| | | 4 | 0.001 | 2313 | 99% Adhesive C/S |
| | | 5 | 0.001 | 1702 | 99% Adhesive C/S |
| | | | 0.002 | 1775 ± 372 | |

The invention has been described with reference to its preferred embodiments. Persons of ordinary skill in the art may appreciate changes and modifications that can be made which do not depart from the scope and spirit of the invention as described above and claimed hereafter.

What is claimed:

1. A method of forming a coating on a prosthetic implant, comprising:
   (i) coating at least a portion of the surface of a prosthetic implant with a coating composition comprising a bismaleimide-triazine resin and a biocompatible plasticizer; and
   (ii) at least partially curing the bismaleimide-triazine resin.

2. The method of claim 1, further comprising adding a thickening agent to the coating composition.

3. The method of claim 1 wherein the biocompatible plasticizer comprises citric acid esters or glyceryl esters.

4. The method of claim 3, wherein the citric acid ester comprises acetyltri-n-butyl citrate, acetyltriethyl citrate, tri-n-butyl citrate, n-butyl phthalyl-n-butyl glycolate, triethyl citrate, acetyltri-n-hexyl citrate, n-butyltri-n-hexyl citrate, tri-n-hexyl trimellitate, monostearyl citrate, or mixtures thereof.

5. The method of claim 3, wherein the glyceryl esters comprise oligo(L-lactate-co-glycerate) or oligo(glycolate-co-glycerate).

6. The method of claims 1 or 2, wherein the coating composition further comprises a radio-opaque composition.

7. The method of claims 1 or 2, wherein the coating composition further comprises hydroxyapatite or β-tricalcium phosphate.

8. The method of claims 1 or 2 wherein the coating composition includes barium sulfate.

9. An at least partially coated prosthetic implant, comprising:
(a) a substrate portion comprising a thermoplastic composition, a thermoplastic composite, a metal, a metallic alloy or a ceramic component; and
(b) a coated surface portion adherent to at least a portion of the surface of the substrate portion, the coated surface portion comprising the reaction product of at least partially curing a composition comprising a bismaleimide-triazine resin, a biocompatible plasticizer and optionally a thickening agent.

10. The orthopedic implant of claim 9, wherein the substrate portion is a polyaryletherketone composite comprising polyetherketone, polyetherketoneketone, or polyetheretherketone.

11. The orthopedic implant of claims 9 or 10, wherein the coated surface comprises a radio-opaque composition.

12. The orthopedic implant of claims 9 or 10, wherein the coated surface comprises hydroxyapatite, or β-tricalcium phosphate.

13. The orthopedic implant of claims 9 or 10 wherein the coated surface further comprises the radio-opaque composition barium sulfate.

14. The orthopedic implant of claim 9, wherein the biocompatible plasticizer comprises citric acid esters or glyceryl esters.

15. The orthopedic implant of claim 14 wherein the citric acid esters comprise acetyltri-n-butyl citrate, acetyltriethyl citrate, tri-n-butyl citrate, n-butyl phthalyl-n-butyl glycolate, triethyl citrate, acetyltri-n-hexyl citrate, n-butyltri-n-hexyl citrate, tri-n-hexyl trimellitate, monostearyl citrate, or mixtures thereof.

16. The orthopedic implant of claim 14, wherein the glyceryl ester comprises oligo(L-lactate-co-glycerate) or oligo(glycolate-co-glycerate).

* * * * *